US012226556B2

(12) United States Patent
Bauer et al.

(10) Patent No.: US 12,226,556 B2
(45) Date of Patent: Feb. 18, 2025

(54) DIALYSIS MACHINE HAVING A HOLDING DEVICE FOR HOLDING AND FIXING AT LEAST ONE ELECTRONIC TERMINAL DEVICE

(71) Applicant: B. Braun Avitum AG, Melsungen (DE)

(72) Inventors: Florian Bauer, Melsungen (DE); Waldemar Janik, Melsungen (DE)

(73) Assignee: B. Braun Avitum AG, Melsungen (DE)

( * ) Notice: Subject to any disclaimer, the term of this patent is extended or adjusted under 35 U.S.C. 154(b) by 300 days.

(21) Appl. No.: 17/631,580

(22) PCT Filed: Aug. 17, 2020

(86) PCT No.: PCT/EP2020/073018
§ 371 (c)(1),
(2) Date: Jan. 31, 2022

(87) PCT Pub. No.: WO2021/032692
PCT Pub. Date: Feb. 25, 2021

(65) Prior Publication Data
US 2022/0313878 A1 Oct. 6, 2022

(30) Foreign Application Priority Data
Aug. 20, 2019 (DE) ...................... 10 2019 122 353.9

(51) Int. Cl.
*A61M 1/14* (2006.01)
*H02J 7/00* (2006.01)

(52) U.S. Cl.
CPC ....... *A61M 1/14* (2013.01); *A61M 2205/8237* (2013.01); *A61M 2205/8243* (2013.01);
(Continued)

(58) Field of Classification Search
CPC ............ A61M 1/14; A61M 2205/8237; A61M 2205/8243; A61M 2205/8256;
(Continued)

(56) References Cited

U.S. PATENT DOCUMENTS 6,146,523 A 11/2000 Kenley et al.
8,798,284 B2 8/2014 Cartwright et al.
(Continued)

FOREIGN PATENT DOCUMENTS

CN 107948370 A 4/2018
CN 108186232 A 6/2018
(Continued)

OTHER PUBLICATIONS

Machine-generated English translation of DE 102012020945, generated on Jun. 14, 2024.*
(Continued)

*Primary Examiner* — Fred Prince
(74) *Attorney, Agent, or Firm* — Christopher A. Rothe; CM Law

(57) ABSTRACT

A holding device for holding and fixing at least one electronic terminal device, in particular of the entertainment electronics type, during a medical treatment, more particularly dialysis treatment. The terminal device is or can be attached to a medical treatment apparatus, such as a dialysis machine, or to a patient bed. The holding device includes an integrated charging unit to supply the held and/or fixed electronic terminal device with power, more particularly from the medical treatment apparatus, with a protection circuit being integrated in the holding device to detect a defect of a terminal device that has just been connected. A charging unit includes an integral power supply unit on a dialysis machine or patient bed having a holding device.

17 Claims, 4 Drawing Sheets

(52) U.S. Cl.
CPC ............... *A61M 2205/8256* (2013.01); *A61M 2209/082* (2013.01); *H02J 7/0029* (2013.01); *H02J 7/0044* (2013.01); *H02J 2310/23* (2020.01)

(58) Field of Classification Search
CPC ............. A61M 2209/082; H02J 7/0029; H02J 7/0044; H02J 2310/23
USPC .......................................... 210/85, 646, 647
See application file for complete search history.

(56) References Cited

U.S. PATENT DOCUMENTS

| | | |
|---|---|---|
| 10,126,759 B2 | 11/2018 | Mueller |
| 2011/0275984 A1 | 11/2011 | Biewer et al. |
| 2014/0121845 A1 | 5/2014 | Mueller |
| 2014/0269553 A1 | 9/2014 | Stein et al. |
| 2015/0234363 A1 | 8/2015 | Yoon et al. |
| 2017/0064251 A1 | 3/2017 | Soneda et al. |
| 2017/0131796 A1 | 5/2017 | Wong et al. |
| 2018/0001010 A1 | 1/2018 | Blümler et al. |
| 2019/0104213 A1 | 4/2019 | Hatch et al. |
| 2023/0270922 A1 | 8/2023 | Crawford et al. |

FOREIGN PATENT DOCUMENTS

| | | | |
|---|---|---|---|
| DE | 102012020945 A1 | 4/2014 | |
| DE | 102019122353 A1 | 2/2021 | |
| JP | 2000504988 A | 4/2000 | |
| JP | 2007243910 A | 9/2007 | |
| JP | 2010523207 A | 7/2010 | |
| JP | 2014126167 A | 7/2014 | |
| JP | 201516691 A | 9/2015 | |
| JP | 2019519331 A | 9/2017 | |
| JP | 2019520907 A | 7/2019 | |
| WO | 2017064251 A1 | 4/2017 | |
| WO | WO-2017064248 A1 * | 4/2017 | .............. A61M 1/16 |
| WO | 2017131796 A1 | 8/2017 | |

OTHER PUBLICATIONS

Search Report received in German Application No. 10 2019 122 353.9 dated Apr. 9, 2020, with translation, 17 pages.
Search Report received in International Application No. PCT/EP2020/073018 dated Nov. 6, 2020, with translation, 5 pages.
Written Opinion received in International Application No. PCT/EP2020/073018 dated Nov. 6, 2020, with translation, 14 pages.
Office Action received in Japanese Application No. 2022-511128 dated May 28, 2024, with translation, 9 pages.

* cited by examiner

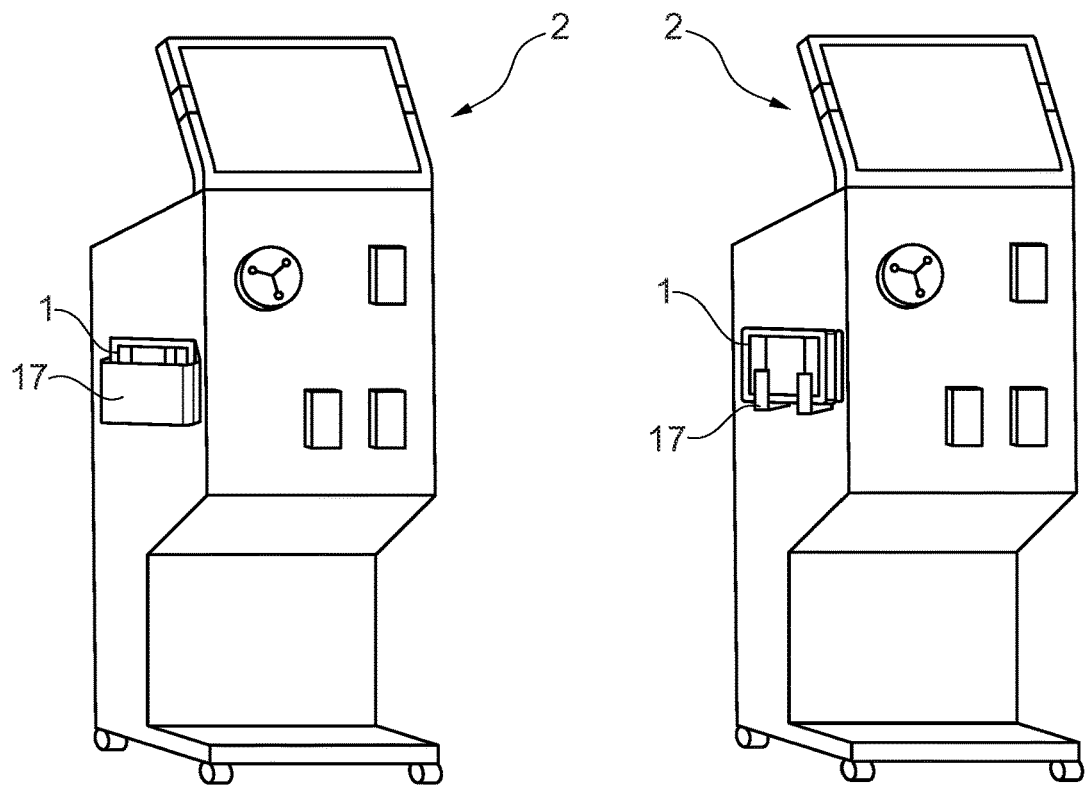
Fig. 6                    Fig. 7
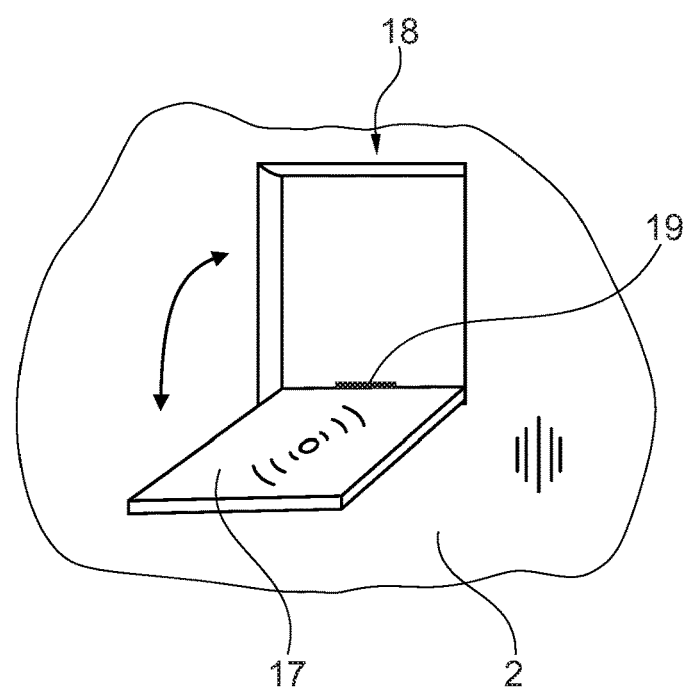
Fig. 8

DIALYSIS MACHINE HAVING A HOLDING DEVICE FOR HOLDING AND FIXING AT LEAST ONE ELECTRONIC TERMINAL DEVICE

CROSS-REFERENCES TO RELATED APPLICATIONS

This application is the United States national phase entry of International Application No. PCT/EP2020/073018, filed Aug. 17, 2020, and claims priority to German Application No. 10 2019 122 353.9, filed Aug. 20, 2019. The contents of International Application No. PCT/EP2020/073018 and German Application No. 10 2019 122 353.9 are incorporated by reference herein in their entireties.

FIELD

The present disclosure relates to a holding device for holding and fixing at least one electronic terminal device during a dialysis treatment with an integrated charging unit.

BACKGROUND

During a dialysis, a patient stays on a bed next to the dialysis machine for about four to five hours. Since a patient must be dialyzed up to three times a week, this results in a large weekly time commitment within the dialysis center. Because of these time constraints, patients sometimes react very irritably if the therapy takes longer than usual. In addition, the schedule is strictly timed, as cabs, for example, are already waiting to take individual patients home.

Most patients spend the weekly 12 to 15 hours watching TV on the TV sets installed in the dialysis center, listening to music, reading books or sleeping. A TV set is usually installed in such a way that three to four patients can/must watch it at the same time and accordingly have to agree on the TV program.

Increasing digitization and the associated widespread availability of mobile terminal devices also does not stop at dialysis center patients. They also make extensive use of mobile electronic devices, such as smartphones, e-book readers and tablets, in particular to make their time during dialysis a little more pleasant.

In particular, the trend toward being able to use more and more services "on-demand" and thus watch series and movies whenever one wants offers attractive opportunities to combine dialysis time with pleasant leisure activities. As a result, it can be expected that more and more people in a dialysis center will make their time more enjoyable with the use of mobile terminal devices.

However, larger media applications, such as streaming/ online watching of movies and series or playing mobile games, for example, sometimes consume a lot of energy/ rechargeable battery power and thus can quickly drain a conventional rechargeable battery of a mobile terminal device. In particular as progress in rechargeable battery development is slower than in the other areas/disciplines of entertainment electronics, the ability to recharge one's device more quickly is becoming more and more important.

Thus, if a patient wants to charge his/her mobile terminal device, he/she must carry along his/her own charger in the form of a power bank/external energy storage medium. Connecting a charger to the dialysis center's own power outlets is prohibited in most cases, as a non-certified device could cause a power failure within the dialysis center or destroy a fuse in the dialysis center in the event of a defect, with corresponding negative or even dangerous effects on the patients receiving treatment at that time. In addition, short circuits triggered by such a device could also result in a fire.

Therefore, a patient depends on the rechargeable battery capacity of his/her device to make the waiting time during the dialysis more pleasant by using his/her own mobile terminal device. If the capacity of the rechargeable battery reaches its minimum and the patient does not have a recharging option with him/her, it is not possible to continue using his/her device. As a result, the patient's state of mind sometimes deteriorates drastically, as he/she is now unable to perform any desired leisure activity. Moreover, in the case of a drained rechargeable smartphone battery, he/she cannot make contact with other people or them with him/her. These people could be relatives or friends, for example, who have to pick up the patient after the therapy and may be late.

Furthermore, a dialysis center is taking a risk should they allow patients to connect their own charger to the in-house power supply system. In particular, low-quality or defective products can, in the worst case, lead to a power failure within the center. Moreover, if the patient is able to use his/her own device, he/she must ensure that a power outlet is located at a suitable distance from his/her dialysis station. In addition, the patient must hold the device in his/her hands at all times in order to be able to watch a series with it, for example. It is often impossible to tell exactly on which side of the machines the patient is. Accordingly, a cable could be distractingly in the way or too short to extend from the socket to the patient.

WO 2017/064 251 A1 describes a medical system that allows a patient to safely power an external electronic terminal device during a treatment. Here, an electrically insulated power outlet is provided on the machine housing so that mobile terminal devices can be charged via a cable.

DE 10 2012 020 945 A1 describes how a mobile terminal device can be attached to a fluid management device to replace a display and input unit. However, the mobile terminal device is then no longer available to the patient for entertainment purposes.

WO 2017 131 796 A1 discloses a multifunctional nurse call system to which a mobile terminal device can be connected. However, no medical devices can be read or controlled with it. Moreover, no wireless power transmission for charging the mobile terminal device is provided in this case.

CN 108 186 232 A describes a patient bed that has a storage area on which mobile terminal devices can be charged wirelessly.

CN 107 948 370 A describes a terminal device holder with integrated rechargeable battery for fixing and charging mobile terminal devices.

SUMMARY

Therefore, the object of the present invention is to avoid or at least reduce the disadvantages arising from the prior art. In particular, a holding device shall be provided which is designed to hold an electronic terminal device during the dialysis treatment and to simultaneously and securely supply it with power.

Said medical treatment apparatuses, preferably dialysis machines, are understood to include, inter alia, conventional hemodialysis or hemodiafiltration devices. Moreover, the holding device can also be used in combination with other devices, such as peritoneal dialysis devices, acute dialysis devices or apheresis devices, etc. Hereinafter, for simplicity, the medical treatment apparatus is replaced by the term dialysis machine.

According to the invention, this object is achieved by a holding device for holding and fixing at least one electronic terminal device, in particular of the entertainment electronics type, during a medical treatment, more particularly dialysis treatment, which is or can be attached to a medical treatment apparatus, such as a dialysis machine, or to a patient bed, having an integrated charging unit, which is provided and designed to supply the held and/or fixed electronic terminal device with power, more particularly from the medical treatment apparatus, with a protection circuit being integrated in the holding device to detect a defect of a terminal device that has just been connected.

In other words, the holding device accommodates the protection circuit which has electrical protection mechanisms that protect the mobile terminal device and the dialysis machine from overvoltage, undervoltage, short circuits or thermal damage, for example temperature sensors. Here, the protection circuit is used to monitor the clamped/employed mobile terminal device to protect both the mobile terminal device, the patient, as well as the dialysis machine and its environment. Placing the protection circuit in the holding device has the advantage that due to this decoupling no damage can be caused to the dialysis machine by the mobile terminal device.

Alternatively or additionally, it is preferred for the holding device to be already supplied with low voltage of e.g. 5V for charging the terminal device. In this way, a protection circuit that preferably only monitors the charging current could be integrated in the treatment device. In case a rechargeable battery is used, two protection circuits would then be used. In this case, a first protection circuit is provided in the holding device for monitoring the charging process of the mobile terminal device and a second protection circuit is provided in the medical treatment device for monitoring the charging process of the rechargeable battery.

In other words, a patient shall be given the opportunity of safely supplying power to his/her mobile terminal device by means of a holding device connected to the machine or to the patient bed. In this case, the installation of a holding device is provided that is connected to the machine or to the patient bed and is used for mobile terminal devices, such as smartphones, tablets, e-readers, etc. In addition to supplying power, the holding device also allows the mobile terminal devices brought along to be charged during the dialysis treatment.

This solution involves the advantage that patients can charge their mobile terminal device at any time, making their time during dialysis treatment more comfortable. Patients do not have to worry about their mobile terminal devices failing due to a lack of rechargeable battery capacity. In addition, the dialysis center does not have to worry about the use of specifically brought chargers on the home network. In other words, this has the advantage of providing an external power supply without compromising safety.

The holding device is preferably designed with a front flap and a rear flap, which are connected to each other via a joint/hinge on one side and can be pivoted relative to each other. The front flap is designed by a frame with a closed rear side. The frame is designed in such a way that it accommodates the mobile terminal device. On the opposite side of the joint, the front flap is connected to the rear flap by a (length-) adjustable bottom. This allows the patient to place the holding device on a flat base/surface with a desired angle.

The adjustable bottom is preferably designed by means of a ribbed/grooved surface or a set screw to flexibly adjust a set-up angle of the mobile terminal device. Accordingly, the set screw is designed to be integrated in the bottom in such a way that it is flexibly shifted and tightened. The shifting of the set screw is provided via a rail integrated in the bottom, for example. In addition, it is provided that the bottom has a corresponding length/depth in order to also use a large set-up angle, preferably greater than 90°, more preferably greater than 120°. The advantage is that the holding device also remains stable on a soft base such as a mattress.

It is preferred for the holding device, the electronic terminal device and the dialysis machine to be designed and intended to communicate with one another in order to transmit data between the dialysis machine and the electronic terminal device, preferably bidirectionally. In other words, the holding device is designed as an intelligent holding device which provides for an exchange of data or a communication link between the dialysis machine and the mobile terminal device.

It is preferred for the data to be transmitted to be treatment-specific data/information. The input and display device has different display elements and buttons for entering and displaying data/information. Accordingly, a display element can, for example, display the progress of the dialysis treatment and a button can be used to call medical personnel.

Furthermore, the data to be transmitted includes e.g. information from the patient on his fluid intake during the dialysis treatment. This information can in turn be entered via buttons on the input and display device. Since one goal of dialysis treatment is to remove excess water from the patient, the fluid intake can be taken into account directly by increasing the ultrafiltration volume by the volume of consumed fluid. Another advantage is that the additionally required ultrafiltration volume can be distributed evenly over the remaining therapy time.

This comfort function that can be integrated, such as reading out the course of therapy, and the direct and immediate transmission of information between the dialysis machine and the mobile terminal device or holding device, offer an efficient dialysis treatment that is more pleasant for the patient.

For example, a button for a beverage with a predetermined volume of up to 150 ml, another button for a medium beverage with a volume between 150 ml and 250 ml, another button for a large beverage with a volume of more than 250 ml (up to 400 ml) can be available on the display device. Of course, it would also be conceivable to directly record the volume of the beverages by a numerical input or by using a button designed as a slider bar.

In addition, it is preferable to deal with the ingestion of food during the treatment in a similar way in order to make adjustments directly. In particular, if the patient consumes/eats e.g. pieces of fruit or pastries or the like, of which it is at least approximately known how much potassium and/or sodium is contained therein, the patient can pass this on to the dialysis machine via the display and input device. This dialysis machine is then designed to adjust the composition of the dialysis fluid in such a way that the amount of potassium and/or sodium and/or another electrolyte contained in fresh dialysis fluid, which is additionally consumed through the food, is diffusively removed again in the further course of treatment.

It is further preferred that the terminal device can also be used for patient identification and thus take over e.g. the function of a patient card known from the prior art. On the basis of this identification, treatment parameters can then be downloaded from the dialysis center's data management system to the dialysis machine, for example. Alternatively, these parameters/this data might also be stored directly on the terminal device from where they are transmitted to the dialysis machine.

It is preferred for the holding device to be provided and designed to clamp a mobile terminal device in order to be brought into different position postures, preferably by means of a swivel arm/holding arm, and to remain in the set position posture. In other words, this means that the holding device preferably has two clamping elements which can be adjusted to terminal devices of different sizes and are designed in such a way that the mobile terminal device can be held and fixed by the holding device due to the pressure exerted on the terminal device by the clamping elements. The clamping elements can be moved manually by the patient by means of position holders which protrude from the edge of the holding device, in order to clamp terminal devices of different sizes. This has the advantage that the method of clamping is gentle on the terminal device and does not leave any damage.

It is advantageous for the holding device to be attached to a multi-joint and pivotable swivel arm/holding arm. In this case, the swivel arm is designed either as part of the dialysis machine or as part of the patient bed. The swivel arm allows the patient to place the mobile terminal device clamped in the holding device in front of him/her in such a way that it does not have to be held or put down.

Furthermore, this has the advantage that the patient does not have to hold the mobile terminal device in his/her hands the entire time since the shape of the holding device is designed in such a way that it can stand on its own and/or be placed on the lap, for example. This ergonomic and comfortable holding device allows patients to comfortably place the device for them without having to hold it the entire time.

It is preferred for a screen of the electronic terminal device to be provided and designed as the input/display device and to be freely accessible to the user and/or patient during a treatment. The patient is given the possibility, by means of this holding device for the mobile terminal device that is connected to the machine or patient bed, to safely supply the device with power and still fix the mobile terminal device in a comfortable and easily accessible position for him/her in order to be able to continue to use it as a means of entertainment.

In this regard, the holding device is designed in such a way that full operation of the mobile terminal device is still ensured for the patient. This has the advantage that his/her overall sensation and quality of dialysis time spent is increased, provided he/she wants to spend his/her time using a mobile terminal device.

It is preferred for the holding device to be provided and designed to supply power to the mobile terminal device via a cable connected to the dialysis machine or the patient bed, or via an energy storage unit, preferably a rechargeable battery. In the case where the holding device has a separate energy storage unit, the energy storage unit is preferably charged between two treatments.

Furthermore, it is preferred for the charging holder to have a wireless charging mechanism/an energy transfer device. The charging holder is preferably attached to one side of the dialysis machine or to the patient bed, preferably its arm support/armrest. In other words, for example, a wireless method, preferably using induction, can be employed for charging the energy storage unit. The charging mechanism can also be attached to the dialysis machine in the form of another holder/charging holder. In this way, the energy storage unit of the holding device can be docked to the charging holder of the dialysis machine between each therapy so as to be recharged for the next therapy.

The charging holder allows the holding device to be attached to the dialysis machine in a frictional and/or interlocking manner. This includes, for example, plug-in connections, clamps or even magnetic connections, a pocket or clamps/hooks into which the holding device is inserted/attached/fixed for charging the energy storage unit integrated therein.

Furthermore, it is preferred for the charging mechanism to be located inside or outside the housing of the dialysis machine and to have at least one coil integrated therein, which is used/needed for wireless energy transmission by means of inductive or resonant inductive coupling. Here, common measures for shielding are provided or implemented so that electromagnetic compatibility is ensured and surrounding medical as well as non-medical devices do not interfere or are not disturbed.

A charging holder attached to a dialysis machine is further preferred. The charging holder for wireless power transmission has an integrated coil that is disposed on the housing of the dialysis machine or on a patient bed and can be folded out via a hinge. When folded out, a mobile terminal device that can be charged by induction (no additional holding device required) or the holding device can be placed on the charging holder for charging. As soon as charging is no longer required, the charging holder can be folded in.

It is preferred for the holding device to comprise at least one integrated circuit. The circuit comprises a charging circuit and a processing circuit and/or a fuse circuit.

In the case where the holding device is attached to the dialysis machine, the fuse circuit is provided within the holding device and includes electrical fuse mechanisms that protect the mobile terminal device and the dialysis machine from overvoltage, undervoltage, short circuits, or thermal damage.

In the case where the holding device is attached to the patient bed, no fuse protection is required between the dialysis machine and the holding device because the power supply of the holding device is provided with the patient bed.

In the case where the holding device is powered by an energy storage unit, electrical fuse mechanisms are located within the holding device to protect the mobile terminal device from overvoltage, undervoltage, short circuits, and/or thermal damage. Furthermore, all the necessary circuits for the correct control of the installed rechargeable battery and its charging circuit are disposed within the holding device. In this case, the invention has the advantage that there is no interfering cable on the holding device and a charging holder provides fast charging without a cable.

Thus, the holding device performs safety monitoring and protects mobile terminal devices and the dialysis machine from electrical or thermal hazards.

In a preferred embodiment of the invention, the charging unit is designed with integrated adapters/charging adapters, for example USB connections, to allow different models of electronic terminal devices to be electrically connected to the charging unit. In other words, this means that the holding device allows, by integrated charging adapters for different standards of the mobile terminal devices, the charging of the mobile terminal devices which are brought along.

It is preferred for the holding device to have a headphone connection. In other words, this means that an external connector/external connection for plugging in headphones is provided on the holding device.

It is preferred for the holding device to be provided and designed to communicate and exchange data with the connected electronic terminal device via NFC (Near Field Communication, an international transmission standard based on RFID technology for contactless exchange of data) and a corresponding app. In other words, the holding device can communicate and exchange information about the course of therapy with the connected mobile terminal device via NFC and a corresponding app. The information entered by the patient, if any, for example whether the patient has consumed fluid during the treatment, can be transmitted directly to the machine for an adjustment of the therapy or therapy parameters, in particular the ultrafiltration volume. The transmission is preferably carried out by radio or Bluetooth. In this way, a function for the staff call can also be integrated into the holding device. Here it is preferred, on the basis of an input at the electronic terminal device about the consumed fluid volume of the patient, to adjust the ultrafiltration volume directly, preferably automatically.

The present invention further relates to a charging unit with an integral/integrated power supply unit on a dialysis machine or a patient bed having a holding device according to any of the preceding aspects. In other words, the charging unit is simultaneously used as a power supply unit on a dialysis machine or a patient bed having a holding device.

In summary, the present invention provides a holding device/terminal device holder in which as many as possible of the common models of mobile devices can be fixed. At the same time, the screen remains free to allow the mobile terminal devices to continue to be operated. Furthermore, it is provided that the fixed terminal devices are supplied with power via integrated adapters within the holding device for various standards. In addition, circuits for electrical and thermal safety (temperature sensors) are located inside the holding device. The holding device can be connected to the machine via a cable and supplied with power. Alternatively, the power supply can also be connected to the bed or realized via a rechargeable battery and a wireless charging holder, which is preferably attached to the machine or to the patient bed.

In this case, the design is chosen such that the holding device can stand on its own and be to placed in various positions, thus eliminating the need for the patient(s) to hold it the entire time. Alternatively, the holding device is attached to a swivel arm which is part of the machine or patient bed. Connections for headphones can additionally be integrated, as can quick-entry keys. The quick input keys can be used, for example, to adjust the volume or to press a forward/backward key.

The system can be expanded by a wireless interface via which the holding device, dialysis machine and mobile terminal device (NFC, Bluetooth, WLAN, or the like) can communicate with one other and exchange information about the course of therapy.

BRIEF DESCRIPTION OF THE DRAWING FIGURES

FIG. 6 is a schematic diagram of the first charging holder attached to a dialysis machine with holding device;

FIG. 7 is a schematic diagram of the second charging holder attached to a dialysis machine with a holding device;

FIG. 8 is a schematic diagram of a third charging holder attached to a dialysis machine;

DETAILED DESCRIPTION

Embodiments of the present disclosure are described below on the basis of the associated drawings. The drawings are merely schematic in nature and are used for the purpose of understanding the invention. The same elements are designated by the same reference signs.

Figure 1:
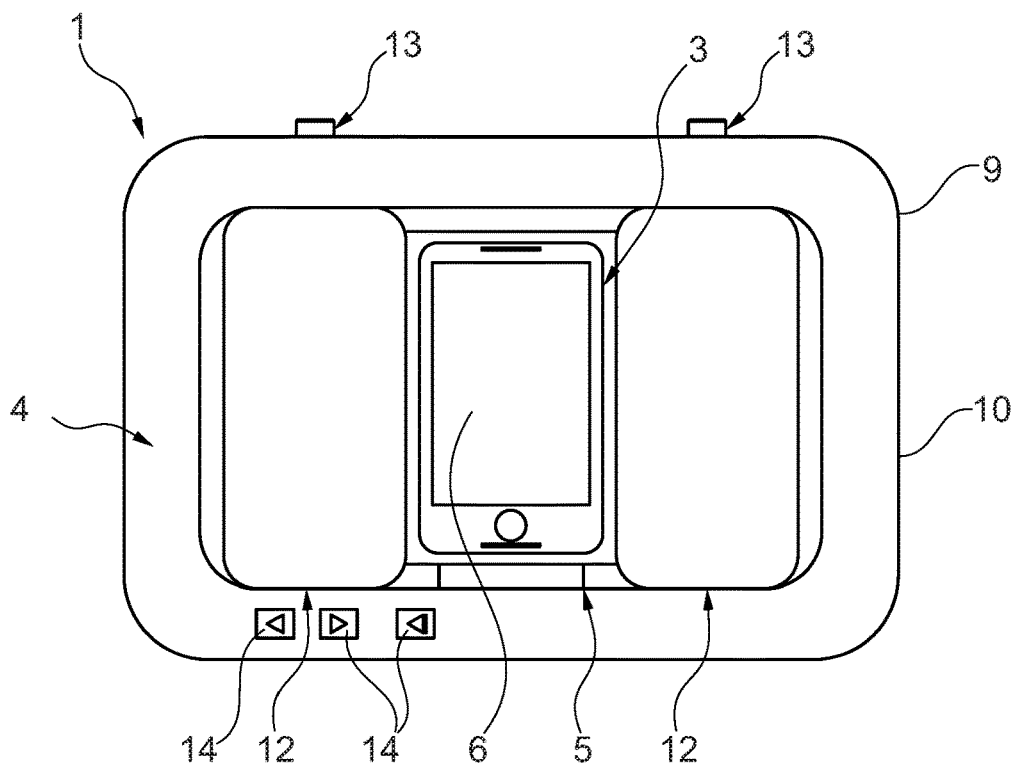
FIG. 1 is a schematic diagram of a holding device in combination with a smartphone.
Figure 2:
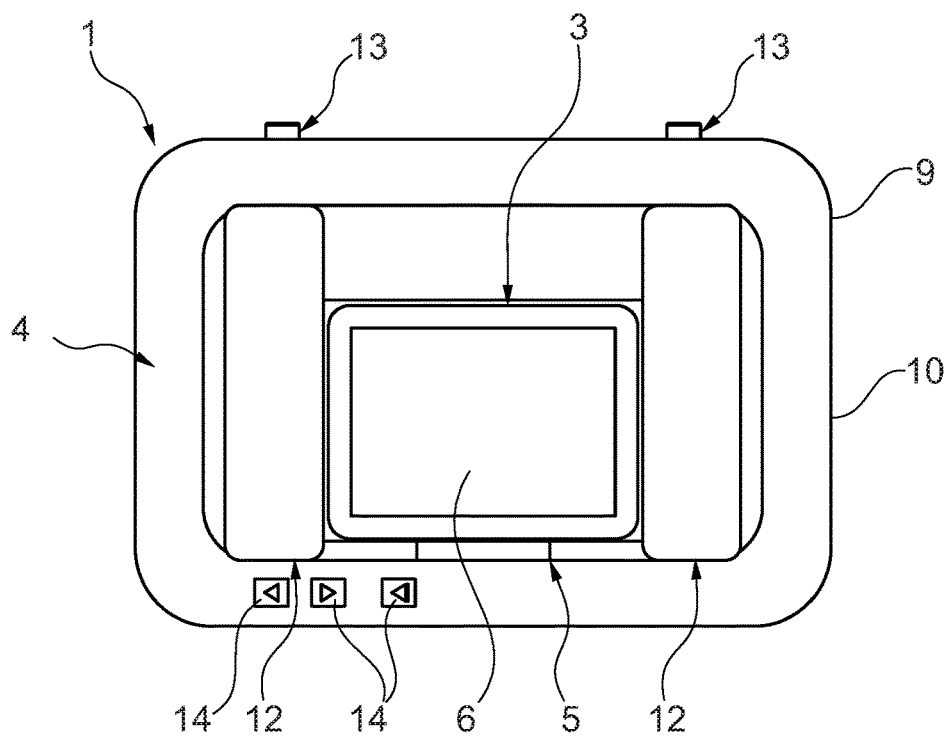
FIG. 2 is a schematic diagram of a holding device in combination with a tablet.

FIG. 1 shows a schematic diagram of a holding device 1 in combination with a smartphone as a mobile terminal device 3, and FIG. 2 shows a schematic diagram of the holding device 1 in combination with a tablet as a mobile terminal device 3. In FIG. 1 and FIG. 2, the holding device 1 for a dialysis machine 2 is provided to hold and fix the mobile terminal device 3.

The holding device 1 can be attached to the dialysis machine 2 according to a first embodiment (see FIG. 9) or to a patient bed according to a second embodiment (not shown). According to the second embodiment, the attachment of the holding device 1 is preferably provided to the armrest/arm support.

The holding device 1, as shown in FIG. 1 and FIG. 2, has a frame 4 with a closed rear side (hereinafter also referred to as front flap). The frame 4 accommodates the mobile terminal device 3, clamping elements 12 and an integrated charging unit 5, which has at least one charging adapter (not shown) to connect the mobile terminal device 3 to the charging unit 5. The display and input device 6 is provided by the display/screen of the mobile terminal device 3. The mobile terminal device 3 is clamped in the holding device 1 by means of at least one clamping element 12, preferably two of them. The two clamping elements 12 are preferably arranged laterally of the mobile terminal device 3, and are designed to adjust to the size of the mobile terminal device 3 to be clamped by lateral shifting.

Alternatively, the use of only one clamping element 12 is also conceivable. As a further alternative, it is conceivable to use at least one clamping element 12 arranged above and/or below the mobile terminal device 3, and the charging unit 5 is accordingly located on one side of the holding device 1. Furthermore, a magnetic holder of the mobile terminal device can additionally or alternatively be provided.

The holding device 1 is designed with a connection 9, preferably for a supply cable. The connection 9 connects the holding device 1 to the dialysis machine 2 according to the first embodiment. In the second embodiment, the cable connects the holding device 1 to the patient bed. In both embodiments, the connection 9 provides the power supply to the holding device 1 to supply power to the held and/or fixed electronic terminal device 3.

The holding device 1 has at least one position holder 13 on the upper edge of the frame 4 of the holding device 1. As shown in FIG. 1, the holding device 1 has two position holders 13. With these position holders 13, it is possible for the patient to adjust clamping elements 12 by moving them so that the mobile terminal device is held and fixed.

The frame 4 of the holding device 1 has at least one quick input key 14. The quick input keys 14 according to FIGS. 1 and 2 are preferably attached to the lower frame 4. The quick input keys 14 can, for example, relate to the volume and/or a forward/backward key. Alternatively, it is also conceivable that one quick input key 14 functions as a nurse call.

In FIGS. 1 and 2, the charging unit 5 can alternatively be designed as a memory unit 11 according to a third embodiment. In the case of the third embodiment, the connection 9 and the associated supply cable are omitted as described later.

Figure 3:
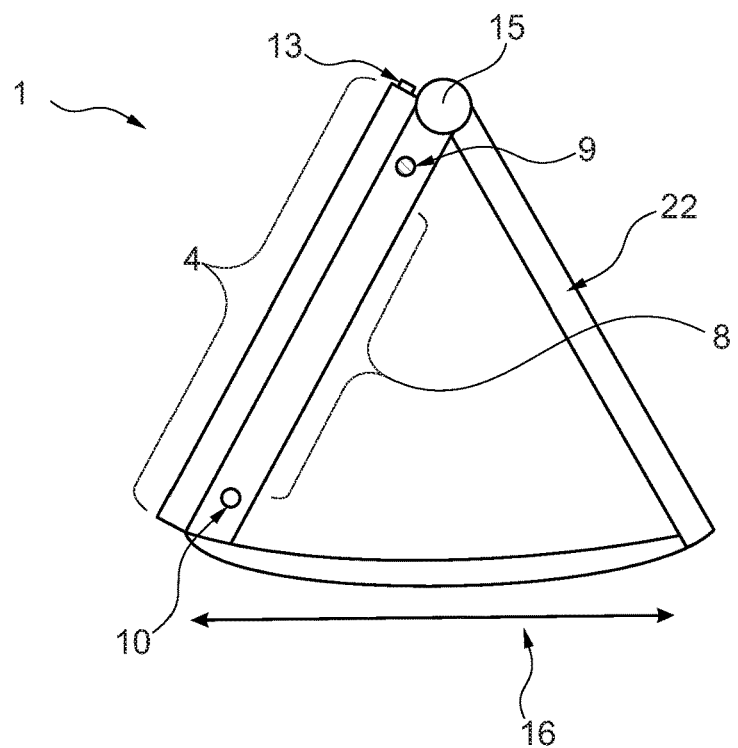
FIG. 3 is a schematic side view of the holding device.

FIG. 3 is a schematic side view of the holding device 1. FIG. 3 shows the frame 4 of the holding device 1. The holding device 1 has a front flap 4 formed by the frame 4 and a rear flap 22. The front flap 4 is formed via a joint 15 with the rear flap 22 which can be pivoted/folded away with respect thereto, and the circuit 8 is accommodated/integrated in the front flap 4. The front flap 4 and the rear flap 22 are connected on the opposite side of the joint 15 via a (length-) adjustable bottom 16. Therefore, parking the holding device 1 according to the third embodiment is possible on a flat base.

The front flap 4 of FIG. 3 shows the headphone connection 10 and the connection 9 for the (supply) cable. A circuit 8 is provided in the front flap 4 at the same time. The circuit 8 has a charging circuit and processing circuit and/or fuse circuit.

FIGS. 4 to 7 below show examples of blood treatment machines/dialysis machines 2 having charging holders 17 for holding devices 1 according to the third embodiment. In this case, the charging holders 17 have wireless charging mechanisms/power transmission devices 18. FIGS. 4 to 8 each show a charging holder 17 on the left side of the dialysis machine 2.

Figures 4, 5:
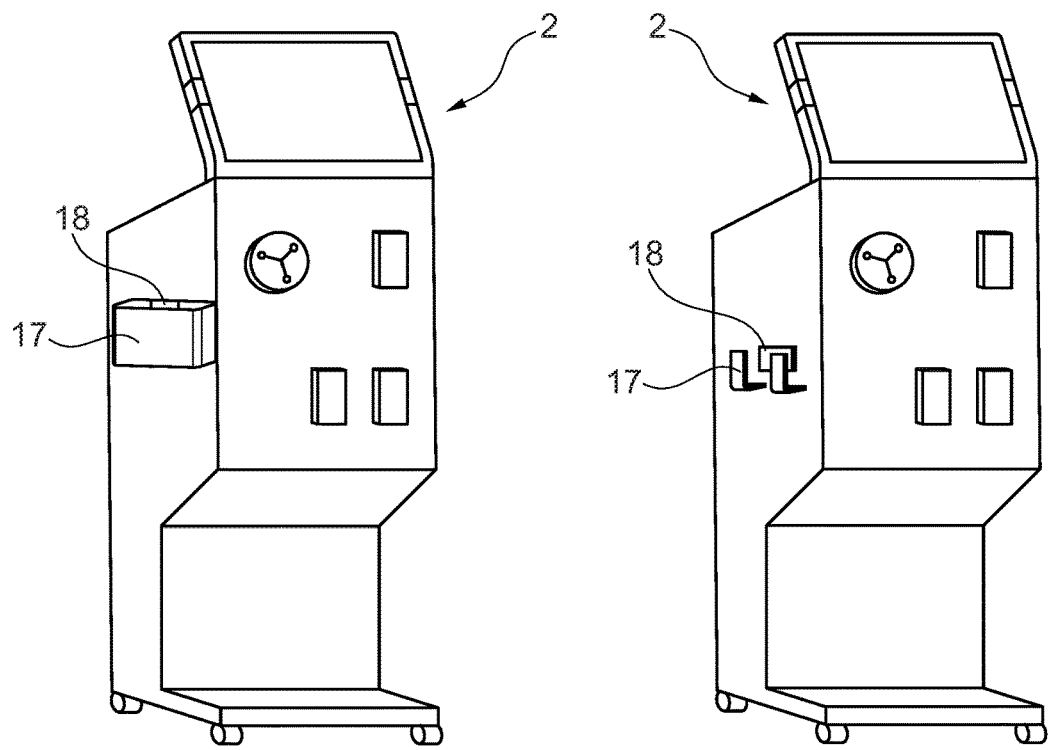
FIG. 4 is a schematic diagram of a first charging holder attached to a dialysis machine.
FIG. 5 is a schematic diagram of a second charging holder attached to a dialysis machine.

Various embodiments are conceivable for the charging holder 17, which allow a frictional and/or interlocking attachment of the holding device 1 to the dialysis machine 2. These include, for example, plug-in connections, clamps or even magnetic connections. FIG. 4 shows a charging holder 17, which is designed as a pocket into which the holding device 1 is placed for charging the energy storage unit 11 integrated therein. FIG. 6 shows the pocket-shaped charging holder 17 with the holding device 1 disposed therein.

FIG. 5 shows a charging holder 17 which is designed as two clamps/hooks into which the holding device 1 is placed for charging the energy storage unit 11 integrated therein. FIG. 7 shows the clamp-/hook-shaped charging holder 17 with the holding device 1 located therein.

The charging mechanism 18 of FIGS. 4 to 7 can be located both inside and outside the housing of the dialysis machine 2 and have at least one coil integrated therein, which is used for the wireless energy transmission by means of inductive or resonant inductive coupling. Here, common measures for shielding are provided or implemented, so that electromagnetic compatibility is ensured and surrounding medical as well as non-medical devices do not interfere or are not disturbed.

The above described charging holders 17 are also conceivable in a similar or identical design on a patient bed, preferably on the arm supports (not shown).

FIG. 8 is a schematic diagram of a third charging holder 17, attached to a dialysis machine 2. As an additional embodiment, FIG. 8 shows an enlarged diagram of a charging holder 17 for wireless energy transmission with an integrated coil, which is located on the housing of the dialysis machine 2 or on a patient bed and can be folded out via a hinge 19. In the folded-out state, a mobile terminal device 3 that can be charged by means of induction can be placed on the charging holder 17 for charging. No additional holding device 1 is necessary here. As soon as charging is no longer necessary, the charging holder 17 can be folded in.

Alternatively, the fold-out charging holder 17 according to FIG. 8 can be designed to charge the holding device 1 as soon as it is resting on the folded-out charging holder 17.

Figure 9:
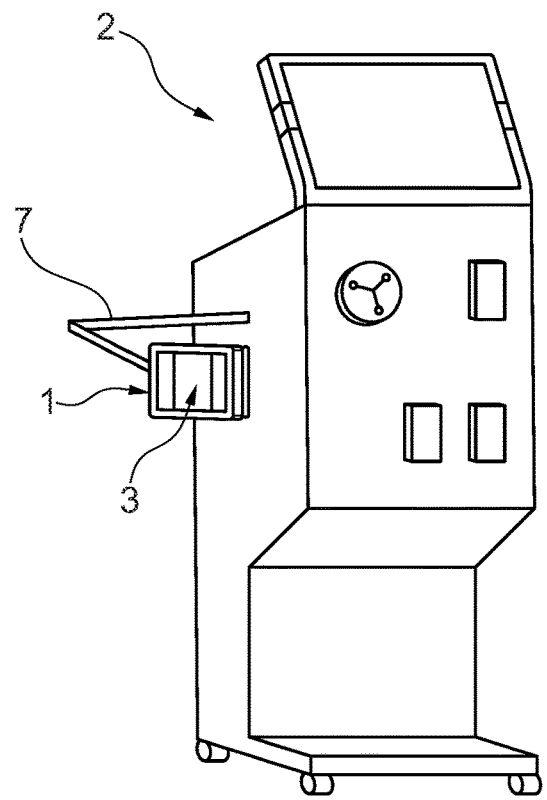
FIG. 9 is a schematic diagram of a holding device with a swivel arm provided on a dialysis machine.

FIG. 9 is a schematic diagram of a holding device 1 with a swivel arm 7 on the dialysis machine 2. The holding device 1 is attached to a multi joint and pivotable swivel arm/holder arm 7. The swivel arm 7 is designed either as part of the dialysis machine 2 according to the first embodiment or as part of the patient bed according to the second embodiment (not shown). The swivel arm 7 allows the patient to place the mobile terminal 3 clamped in the holding device 1 in front of him/her in such a way that it does not have to be put down or held by him/her.

Figure 10:
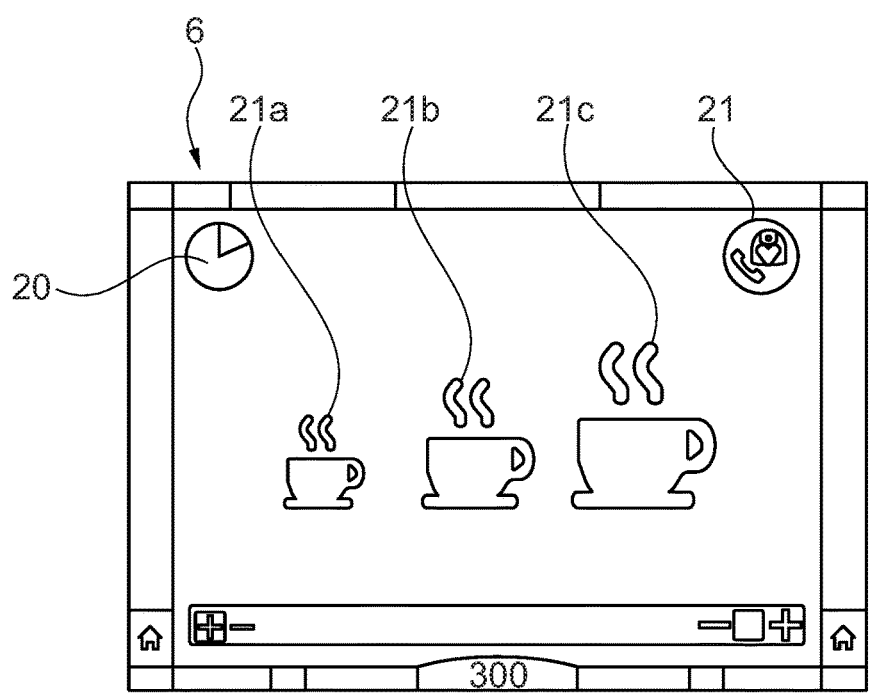
FIG. 10 is a schematic diagram of the user surface of the display and input device.

FIG. 10 is a schematic diagram of the user surface of the display and input device 6. FIG. 10 shows an example of a possible user surface of an app that is executed on the mobile terminal device 3. The user surface has various display elements 20 and buttons 21. For example, the display element 20 shows the progress of the dialysis treatment. The button 21 can be used to call the medical staff.

Furthermore, it is possible to use the buttons 21a, b, c to report a fluid intake during a dialysis treatment to the dialysis machine 2. In FIG. 10, the buttons 21a, b, c are shown as cups of coffee of different sizes, each representing a specific amount of liquid. In this way, the patient can report the amount of consumed liquid to the dialysis machine by tapping the cup of corresponding size.

A similar representation is conceivable for food, for example. In this case, the patient can preferably also enter which food he has consumed so that the dialysis treatment can be adjusted to the correspondingly consumed electrolytes.

The invention claimed is:

1. A holding device of a dialysis machine for holding and fixing at least one electronic terminal device during a dialysis treatment, the holding device comprising:
   a charging unit; and
   a protection circuit,
   the holding device being attached or attachable to the dialysis machine,
   the charging unit being integrated in the holding device and configured to supply the at least one electronic terminal device with power, and
   the protection circuit being integrated in the holding device and configured to detect a defect in the at least one electronic terminal device after it is connected.

2. The holding device according to claim 1, wherein the at least one electronic terminal device and the dialysis machine are configured to communicate with each other in order to transmit data between the dialysis machine and the at least one electronic terminal device by an input and display device of the at least one electronic terminal device.

3. The holding device according to claim 1, wherein the at least one electronic terminal device comprises a mobile terminal device, and
   wherein the holding device is configured to clamp the mobile terminal device in a set position posture and allow the mobile terminal device to be brought into different position postures.

4. The holding device according to claim 1, wherein the holding device is configured such that a screen of the at least one electronic terminal device is provided and designed as an input/display device that is freely accessible to a user and/or a patient during a treatment.

5. The holding device according to claim 1, wherein the holding device comprises at least one circuit that is integrated in the holding device, the at least one circuit comprising a processing and charging circuit.

6. The holding device according to claim 1, wherein the charging unit is designed with integrated adapters/charging adapters to electrically connect different models of electronic terminal devices to the charging unit.

7. The holding device according to claim 1, wherein the holding device includes a headphone connection.

8. The holding device according to claim 1, wherein the holding device is configured to communicate and exchange data with the at least one electronic terminal device via NFC and a corresponding app.

9. The holding device according to claim 1, wherein the holding device is configured to supply the at least one electronic terminal device with power via a connection for a cable, which is connected to the dialysis machine or the patient bed, or via an energy storage unit.

10. A charging unit comprising an integral power supply unit on a dialysis machine with a holding device according to claim 1.

11. The holding device according to claim 1, wherein the holding device comprises a frame configured to surround and hold a mobile terminal device.

12. The holding device according to claim 11, wherein the holding device comprises one or more clamping elements positioned laterally between the frame and the mobile terminal device, wherein the one or more clamping elements are movable to adjust to a size of the mobile terminal device.

13. The holding device according to claim 12, wherein the one or more clamping elements are slidable within the frame.

14. The holding device according to claim 13, wherein the one or more clamping elements comprise a first clamping element configured to hold a first side of the mobile terminal device, and a second clamping element configured to hold a second side of the mobile terminal device, the second side being opposite the first side.

15. The holding device according to claim 11, wherein the holding device further comprises a rear flap movably connected to the frame between a first position to enclose a rear side of the mobile terminal device, and a second position to allow removal of the mobile terminal device from the frame.

16. The holding device according to claim 15, wherein the rear flap is pivotally connected to the frame.

17. The holding device according to claim 11, wherein the frame comprises a nurse call key.

* * * * *